United States Patent [19]

Abrahamsén et al.

[11] Patent Number: 5,721,114
[45] Date of Patent: Feb. 24, 1998

[54] EXPRESSION SYSTEM FOR PRODUCING APOLIPOPROTEIN AI-M

[75] Inventors: Lars Abrahamsén, Stockholm; Erik Holmgren, Lidingö ; Christina Kalderén, Stockholm; Mats Lake, Lidingö ; Åsa Mikaelsson, Stockholm; Torsten Sejlitz, Solna, all of Sweden

[73] Assignee: Pharmacia & Upjohn Aktiebolag, Stockholm, Sweden

[21] Appl. No.: 448,606

[22] PCT Filed: Dec. 9, 1993

[86] PCT No.: PCT/SE93/01061

§ 371 Date: Aug. 25, 1995

§ 102(e) Date: Aug. 25, 1995

[87] PCT Pub. No.: WO94/13819

PCT Pub. Date: Jun. 23, 1994

[30] Foreign Application Priority Data

Dec. 11, 1992 [SE] Sweden ................................. 9203753

[51] Int. Cl.$^6$ ................ C12P 21/06; C12N 15/00; C12N 1/20; C07H 21/04
[52] U.S. Cl. ............... 435/69.1; 435/320.1; 435/252.3; 530/359; 536/23.5
[58] Field of Search ..................... 435/252.33, 69.1, 435/71.1, 252.3, 252.8, 320.1; 530/350, 359; 536/23.1, 23.5

[56] References Cited

FOREIGN PATENT DOCUMENTS 0 267 703 A1  5/1988  European Pat. Off. .
0 345 155 A1  12/1989 European Pat. Off. .
WO 90/12879  11/1990 WIPO .
WO 91/06655  5/1991  WIPO .
WO 93/12143  6/1993  WIPO .

OTHER PUBLICATIONS

Franceschini et al., A–I$_{Milano}$ Apoprotein, J. Clin. Invest., vol. 66, (1980), pp. 892–900.

Badimon et al., Regression of Atherosclerotic Lesions by High Density Lipoprotein Plasma Fraction in the Cholesterol–fed Rabbit, J. Clin. Invest., vol. 85 (1990), pp. 1234–1241.

Moguilevsky et al., Production of Human Recombinant Proapolipoprotein A–I in *Escherichia coli*; Purification and Biochemical Characterization, DNA, vol. 8, No. 6 (1989), pp. 429–436.

Isacchi et al., Mature apolipoprotien AI and its precursor proApoAI: influence of the sequence at the 5' end of the gene on the efficiency of expression in *Escherichia coli*, Gene, vol. 81 (1989), pp. 129–137.

*Primary Examiner*—Robert A. Wax
*Assistant Examiner*—Tekchand Saidha
*Attorney, Agent, or Firm*—Pollock, Vande Sande & Priddy

[57] ABSTRACT

The invention relates to an expression system giving high extracellular production of apolipoprotein AI-M (Milano) using *E. coli* and comprises a plasmid carrying an origin of replication, an inducible promoter sequence, a DNA sequence coding for a signal peptide, a DNA sequence coding for apolipoprotein AI-M, and a transcription terminator. The invention also relates to a method of producing apolipoprotein AI-M using the expression system.

25 Claims, 9 Drawing Sheets

```
                Eco RI           Bbs I                        Nco I
             5'-AATTCAGAAGACACCGCGGACGAGCCACCGCAGAGCC      -3'
             3'-    GTCTTCTGTGGCGCCTGCTCGGTGGCGTCTCGGGTAC-5'
                AsnSerGluAspThrAlaAspGluProProGlnSerPro
                                 -1 +1
```

FIG. 1

```
                Dra IIIΔ             Hind III
             5'-    GTAATAAGGATCCA      -3'
             3'-GGTCATTATTCCTACCTTCGA-5'
                    GlnEndEnd
```

FIG. 2

The DNA segment NotI-HindIII of pKP683 and deduced amino acid sequence of Apo A1-M.

GCGGCCGCGGCTAATTGACATGGGCTATTTTGGATGATAACGAGGCGCAAAAATGAAAAAGACAGCTATCGCGATTGCAGTGGCA
                          MetLysLysThrAlaIleAlaAlaValAla

CTGGCTGGTTTCGCTACCGTAGCGAACGGGACGAGCCACCGCAGAGCCCATGGGATCGAGTGAAGGACCTGGCCACTGTGTAC
LeuAlaGlyPheAlaThrValAlaAsnAlaAspAspSerProProGlnSerProTrpAspArgValLysAspLeuAlaThrValTyr
          -1 +1

GTGGATGTGCTCAAAGACAGCGGCAGAGACTATGTGTCCCAGTTTGAAGGCTCCGCCTTGGGAAAACAGCTAAACCTAAAGCTC
ValAspValLeuLysAspSerGlyArgAspTyrValSerGlnPheGluGlySerAlaLeuGlyLysGlnLeuAsnLeuLysLeu

CTTGACACAACTGGGACAGCGTGACCTCCACCTTCAGCAAGCTGCGCGAACAGCTCGGCCTGTGACCCAGAGTTCTGGATAAC
LeuAspThrThrGlyGlnAlaCysLeuLysGlnLeuGlnGluArgLeuGlyProValThrGlnGluPheTrpAspAsn

CTGGAAAAGGAGACAGAGGGCCTGAGGCAGGAGATGAGCAAGGATCTGGAGGAGGTGAAGGCCAAGGTGCAGCCCTACCTGGAC
LeuGluLysGluThrGluGlyLeuArgGlnGluMetSerLysAspLeuGluGluValLysAlaLysValGlnProTyrLeuAsp

GACTTCCAGAAGAAGTGGCAGGAGGAGATGGAGCTCTACCGCCAGAAGGTGGAGCCGCTGCGCGCAGAGCTCCAAGAGGGCGCG
AspPheGlnLysLysTrpGlnGluGluMetGluLeuTyrArgGlnLysValGluProLeuArgAlaGluLeuGlnGluGlyAla

CGGCAGAAGCTGCACGAGCTGCAAGAGAAGCTGAGCCCACTGGGCGAGGAGATGCGCGACCGCGCCCATGTGGACGCG
ArgGlnLysLeuHisGluLeuGlnGluLysLeuSerProLeuGlyGluGluMetArgAspArgAlaArgAlaHisValAspAla

CTGCGCACGCATCTGGCCCCCTACAGCGACGAGCTGCGCCAGCGAGCATCTGAGCACGCTCAGCGAGAAGGCCAAGCCCGCTCGAGGACCTC
LeuArgThrHisLeuAlaProTyrSerAspGluLeuArgLysArgLeuAlaAlaArgLeuGluAlaLeuLysGluAsnGlyGly

GCCAGACTGGCCGAGTACCACGCCAAGGCCACCGAGCATCTGAGCACGCTCAGCGAGAACACGCTCAGCGAAGGCCAAGCCCGCGCTCGAGGACCTC
AlaArgLeuAlaGluTyrHisAlaLysAlaThrGluHisLeuSerThrLeuSerPheLysSerPheLeuSerAlaLeuGluGluTyrThrLysLysLeuAsnThr

CGGCAAGGCCTGCTGCCCGTGCTGGAGAGCTTCAGGGTGCAGTTTCTGGAGGCGCTCTGAGGCGTACACTAAGAGCTCAACACC
ArgGlnGlyLeuLeuProValLeuGluSerPheLysValGlnPheLeuGluAlaLeu

CAGTGAGGCGCCCGCGCCCGGCCCCCCCTTCCGGTGCTCAGAATAAACGTTTCCAAAGTGGGAAAAAAAAAAAAAAAAA
Gln

AAAAAAAAAAACTGGATCCGTCGACCTGCAGCCAAGCTT

Translated Mol. Weight of Apo A1-M = 28025.33 +1 = N-terminal amino acid of Apo A1-M

FIG. 3

The DNA segment NotI-HindIII of pKP764 and deduced amino acid sequence of Apo AI-M.

```
GCGGCCGCGGCTAATTGACATGGCGTATTTTGGATGATAACGAGGGCAAAAAATGAAAAAGACAGCTATCGCGATTGCAGTGGCA
                                        MetLysLysThrAlaAlaIleAlaAlaValAla
                                                                    -1 +1

CTGGCTGGTTTCGCTACCGTAGCGAACGCGGACGAGCCACCGCAGAGCCCATGGGATGAGTGAAGGACCTGGCCACTGTGTAC
LeuAlaGlyPheAlaThrValAlaAsnAlaAspGluProProGlnSerProTrpAspArgValLysAspLeuAlaThrValTyr
                                                           -1 +1

GTGGATGTGCTCAAAGACAGCGGCAGAGACTATGTGTCCCAGTTTGAAGGCTCCGCCCTTGGGAAAACAGCTAAACCTAAAGCTC
ValAspValLeuLysAspSerGlyArgAspTyrValSerGlnPheGluGlySerAlaLeuGlyLysGlnLeuAsnLeuLysLeu

CTTGACAACTGGGACACAGCTGACCTCCACCTTCAGCAAGCTGCCGAACAGCTCCGGCCCTGTGACCCAGGAGTTCTGGGATAAC
LeuAspAsnTrpAspThrSerThrPheSerLysLeuArgGluGlnLeuGlyProValThrGlnGluPheTrpAspAsn

CTGGAAAAGGAGACAGAGGGCCTGAGGCAAGGAGATGAGCAAGGATCTGGAGGGGAGGTGAAGGCCAAGGTGCAGCCCTACCTGGAC
LeuGluLysGluThrGluGlyLeuArgGlnGluMetSerLysAspLeuGluGluValLysAlaLysValGlnProTyrLeuAsp

GACTTCCAGAAGAAGTGGCAGGAGGAGATGGAGCTCTACCGCCAGAAGGTGGAGCCGCTGCGCGCAGAGCTCCAAGAGGGCGCG
AspPheGlnLysLysTrpGlnGluGluMetGluLeuTyrArgGlnLysValGluProLeuArgAlaGluLeuGlnGluGlyAla

CGGCAGAAGCTGCACGAGCTGCAAGAGAAGCTGAGCCCACTGGGCGAGGAGATGCGCGACCGCGCGCGCGCCATGTGGACGCG
ArgGlnLysLeuHisGluLeuGlnGluLysLeuSerProLeuGlyGluGluMetArgAspArgAlaArgAlaHisValAspAla

CTGCGCACGCATCTGGCCCCCTACAGCGACGAGCTGCGCCAGTGCTTGGCCGCCAGTGTTGCGCCTTGAGGCTTCTCAAGGAGAACGGCGGC
LeuArgThrHisLeuAlaProTyrSerAspGluLeuArgGlnCysLeuAlaAlaArgLeuGluAlaLeuLysGluAsnGlyGly

GCCAGACTGGCCGAGTACCACGCCAAGGCCACCGAACATCTGAGCACGCTGAGCGAGAAGGCCAAGCCCGGCCTCGAGGACCTC
AlaArgLeuAlaGluTyrHisAlaLysAlaThrGluHisLeuSerThrLeuSerGluLysAlaLysProAlaLeuGluAspLeu

CGCCAAGGGCTGCTGCCCGTGCTGGAGAGCTTCAAGGTGAGCTTCCTGAGCGCTCTCGAGGAGTACACTAAGAAGCTCAACACC
ArgGlnGlyLeuLeuProValLeuGluSerPheLysValSerPheLeuSerAlaLeuGluGluTyrThrLysLysLeuAsnThr

CAGTAATAAGGATCCAAGCTT
Gln
```

Translated Mol. Weight of Apo A1-M = 28025.33     +1 = N-terminal amino acid of Apo A1-M

FIG. 4

EXPRESSION SYSTEM FOR PRODUCING APOLIPOPROTEIN AI-M

FIELD OF THE INVENTION

The present invention relates to an expression system yielding high levels of protein in the culture medium of *Escherichia coli* to produce Apolipoprotein AI Milano (Apo AI-M). The product may be used for the treatment of atherosclerosis and cardiovascular disease.

BACKGROUND OF THE INVENTION

The clear correlation between elevated levels of serum cholesterol and the development of coronary heart disease (CHD) has been repeatedly confirmed, based on epidemiological and longitudinal studies. The definition, however, of complex mechanisms of cholesterol transport in plasma, has allowed the recognition of a selective function of circulating lipoproteins in determining the risk for CHD.

There are, in fact, four major circulating lipoproteins: chylomicrons (CM), very low density (VLDL), low density (LDL) and high density (HDL) lipoproteins. While CM constitute a short-lived product of intestinal fat absorption, VLDL and, particularly, LDL are responsible for the cholesterol transport into tissues, among these, also into the arterial walls. In contrast, HDL are directly involved in the removal of cholesterol from peripheral tissues, carrying it back either to the liver or to other lipoproteins, by a mechanism known as "reverse cholesterol transport" (RCT).

The "protective" role of HDL has been confirmed in a number of studies (e.g. Miller et al. (1977) Lancet 965–968 and Whayne et al. (1981) Atherosclerosis 39: 411–419). In these studies, the elevated levels of LDL, less so of VLDL, are associated with an increased cardiovascular risk, whereas high HDL levels seem to confer cardiovascular protection. The protective role of HDL has been further strongly supported by the in vivo studies, showing that HDL infusions into rabbits may hinder the development of cholesterol induced arterial lesions (Badimon et al. (1989) Lab. Invest 60: 455–461) and/or induce regression of these same (Badimon et al. (1990) J. Clin. Invest. 85: 1234–1241).

Recent interest in the study of the protective mechanism(s) of HDL has been focused into apolipoprotein AI (Apo AI), the major protein component of HDL. High plasma levels of Apo AI are associated with reduced risk of CHD and presence of coronary lesions (Maciejko et al. (1983) N. Engl. J. Med. 309: 385–389, Sedlis et al. (1986) Circulation 73: 978–984).

Human apolipoprotein AI-Milano (Apo AI-M) is a natural variant of Apo AI (Weisgraber et al. (1980) J. Clin. Invest 66: 901–907). In Apo AI-M the amino acid Arg173 is replaced by the amino acid Cys173. Since Apo AI-M contains one Cys residue per polypeptide chain, it may exist in a monomeric or in a dimeric form. These two forms are chemically interchangeable, and the term Apo AI-M does not, in the present context, discriminate between these two forms. On the DNA level the mutation is only a C→T transition, i.e. the codon CGC changed to TGC. However, this variant of Apo AI is one of the most interesting variants, in that Apo AI-M subjects are characterized by a remarkable reduction in HDL-cholesterol level, but without an apparent increased risk of arterial disease (Franceschini et al. (1980) J. Clin. Invest 66: 892–900). By examination of the genealogic tree, these subjects appear to be "protected" from atherosclerosis. Human mature Apo AI and Apo AI-M consist of 243 amino acids. They are synthesized as precursor proteins, preproApo AI and preproApo AI-M of 267 amino acids. The 18 amino acid prepeptide is cleaved off in the secretion machinery leaving a proprotein with an extension of 6 amino acids. ProApo AI and proApo AI-M are then converted to the mature forms by a plasma proteolytic activity.

Attempts have been made to produce human Apo AI by way of recombinant DNA technology. In the European patent publication No. 0267703 the preparation of Apo AI from *E. coli* is described. The process describes a chimeric polypeptide where the Apo AI moiety is fused to the N-terminal amino acid residues of β-galactosidase or to one or more IgG-binding domains of Protein A, or to the prosequence of human Apo AI.

The expression of Apo AI and Apo AI-M in yeast strains and the use of the produced components in the treatment of atherosclerosis and cardiovascular diseases is disclosed in WO90/12879. The genes encoding the Apo AI and Apo AI-M were provided with DNA sequences encoding yeast recognizable secretion (including a modified MF alpha-1 leader sequence) and processing signals fused upstream to the gene for the mature proteins.

An *E. coli* system producing Apo AI is described in Hoppe et al. (1991) J. Biol. Chem. 372: 225–234. Expression levels described in this system are in the range between 0.3–4.8 mg per liter culture medium. The system is based on intracellular expression.

Apo AI has also been produced as a fusion protein to β-galactosidase in an intracellular expression system (Lorenzetti et al. (1986) FEBS letters 194: 343–346). The production levels were about 5 mg/l bacterial culture. In this study the influence of the 5' end of the gene on the efficiency of expression in *E. coli* was analyzed. The lacZ gene has been used as a marker for the analysis of Apo AI expression in *E. coli*. The lacZ gene was fused to the 3' end of the Apo AI (Isacchi et al. (1989) Gene 81: 129–137).

The previously disclosed production levels of about 5 mg per liter growth medium for apolipoprotein A1 and apolipoprotein A1-M are too low to make them commercially attractive.

An expression system for the secretory production of apolipoprotein E is described in EP-A-345 155. In this system apolipoprotein E is produced in *E. coli*, whereafter it can be recovered in the periplasm. A yield of up to 0.15–0.45 g per liter is predicted but not demonstrated.

SUMMARY OF THE INVENTION

The purpose of the present invention is to provide for the production by way of recombinant DNA technology of apolipoprotein A1-M (Milano), hereinafter Apo AI-M, in considerably higher yields than those previously obtained. In accordance with the invention it has surprisingly been found that up to about 1000 times more Apo AI-M per liter, i.e. up to at least 4.5 g/liter, is obtained with an inducible expression system in *E. coli* where the Apo AI-M is secreted into the bacterial culture medium, from which the product can be purified by conventional biochemical methods.

A characteristic feature of the invention is an inducible promoter regulating a structural gene consisting of the gene for Apo AI-M headed by a signal sequence enabling the peptide to be secreted into the growth medium. After induction the system is also characterized by an unusual high expression level, in the range of 1.5 g–4.5 g Apo AI-M per liter of growth medium. To achieve an optimal product quality, however, harvest may be performed before the maximum yield is reached.

Biochemical analysis has shown that the N- and C-terminal amino acid sequence and the total amino acid composition of the protein produced is identical to human Apo AI-M, isolated from plasma. Circular dichroic spectrum analysis suggests similar folding of the recombinant Apo AI-M and human Apo AI.

One aspect of the present invention thus relates to a novel expression vector giving extracellular production of Apo AI-M using *E. coli*, which vector comprises a plasmid carrying a suitable origin of replication, an inducible promoter sequence, a DNA sequence coding for a signal peptide, a DNA sequence coding for Apo AI-M, and a transcription terminator.

Suitable basic plasmids to be modified in accordance with the invention may be selected from well known plasmids previously described and used in recombinant methods.

The term Apo AI-M as used herein is to be interpreted in a broad sense and is also meant to comprise functional variants and fragments of the Apo AI-M protein. The DNA-sequence coding for Apo AI-M may be a cDNA sequence coding for the prepro-protein, the pro-protein or, preferably, the mature protein.

Strong inducible *E. coli* promoters are per se well known in the art. As examples may be mentioned the lac promoter which is induced by IPTG (isopropyl-β-D-thiogalactoside), the trp promoter which is repressed by tryptophan and induced by 3-indolyl acetic acid, the trc or tac promoter (hybrids between the trp and lac promoters) which can be induced by IPTG, and the lambda-$P_L$ or lambda-$P_R$ promoters which, in combination with the temperature sensitive lambda repressor cI857, can be induced at temperatures above 30° C., as well as functional derivatives of these promoters. A currently preferred promoter is the trc promoter.

Signal peptides that may be used in the invention are well known in the art and may readily be selected for by the skilled person once he has become informed of the present invention. As an example may be mentioned derivatives of the ompA signal sequence.

Terminators that may be used in the invention may readily be selected for by the skilled person from those well known in the art.

Another aspect of the invention relates to an *E. coli* host organism transformed with the expression vector, i.e. an expression system. Suitable *E. coli* strains are readily apparent to the skilled person.

Still another aspect of the invention relates to a method of producing Apo AI-M, comprising the steps of:

cultivating the transformed host organism in a growth medium, inducing expression of the Apo AI-M in the logarithmic growth phase before the stationary phase is attained, and separating the product from the growth medium.

The proper times for induction, optional temperature change and harvest are chosen as decribed below.

In one embodiment, the cultivation is started at a low temperature of from about 29° to about 31° C., preferably at about 30° C., and the temperature is then raised (in the logarithmic growth phase) to about 37° C. before the stationary growth phase is attained. This temperature raise may be performed in connection with the induction of the expression vector, but may also be effected before or after the induction, say about 3 hours before or after the induction.

Preferably, expression of the Apo AI-M product is induced, and the temperature raised, when an optical density (O.D.) of at least 50 has been attained, for example an O.D. in the range of about 50 to about 100. In the present context, this normally means that induction and temperature raise is effected at between about 15 hours and 20 hours from the start of the cultivation.

In another embodiment, the fermentation is performed at a constant temperature, for example in the range of from about 25° to about 37° C.

The harvest is preferably performed at the optimum cell culture state.

The growth medium preferably comprises yeast extract, optionally supplemented with tryptone. Optionally, the production medium is free from antibiotics.

BRIEF DESCRIPTION OF THE DRAWINGS

FIG. 1 shows the two oligonucleotides used for the fusion of the cDNA copy of the Apo AI-M gene to DNA fragments encoding bacterial signal sequences. The nucleotide sequences of the oligonucleotides SEQ ID No. 1, the unique restriction enzyme cleavage sites Eco RI, Bbs I and Nco I and the deduced amino acid sequence SEQ ID No. 2 around the presumed *E. coli* signal peptidase cleavage site (−1 +1) are also indicated. The amino terminal of Apo AI-M is indicated by +1.

FIG. 2 shows the two oligonucleotides used for the construction of new stop codons for the plasmid pKP764. The nucleotide sequence SEQ ID No. 3 with the deduced carboxyl terminal amino acid of Apo AI-M and the two new stop codons TAA, TAA are shown SEQ ID No. 4.

FIG. 3 shows the 957 bp DNA segment SEQ ID No. 5 (Not I - Hind III) of the plasmid pKP683 with the deduced amino acid sequence SEQ ID No. 6 and molecular weight of the translated protein Apo AI-M. The amino terminal amino acid of Apo AI-M is indicated by +1. The unique cysteine (Cys173), which is essential for the dimerisation of Apo AI-M, is underlined.

FIG. 4 shows the 856 bp DNA segment SEQ ID No. 7 (Not I - Hind III) of the plasmid pKP764 with the deduced amino acid sequence SEQ ID No. 6 and molecular weight of the translated protein Apo AI-M. The amino terminal amino acid of Apo AI-M is indicated by +1. The unique cysteine (Cys173), which is essential for the dimerisation of Apo AI-M, is underlined.

DETAILED DESCRIPTION OF THE INVENTION

Figure 5:
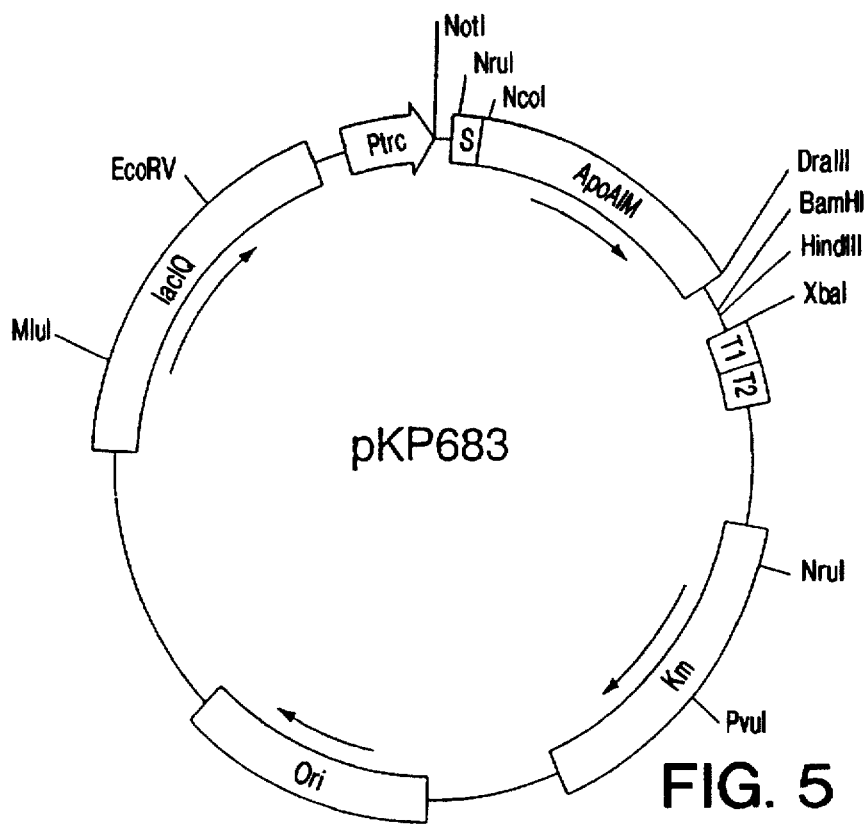
FIG. 5 shows the expression vector pKP683. The important structural and regulatory elements are outlined as boxes with arrows indicating the direction of translation and replication, respectively. Some of the unique restriction enzyme sites are indicated outside the plasmid circle. Also the two sites of Nru I are indicated. The abbreviations inside the boxes are: S, signal sequence; Apo AI-M, Apolipoprotein AI-Milano; T1 and T2, tandem repeats of Rho independent terminators from the bacteriophage fd; Km, the kanamycin resistance marker originating from the transposon Tn903; Ori, origin of replication; lacIQ, (lacI$^q$) the gene for the constitutively produced lac-repressor; Ptrc, the hybrid trp/lac promoter trc.

In the following non-limiting Examples, in which the invention is described in more detail, by way of example only, the construction of plasmid vectors for direct secretion of Apo AI-M SEQ ID No. 6 to the *E. coli* periplasmic space and excretion to the growth medium at a very high level will be described as well as the production of Apo AI-M in bioreactors.

EXAMPLE 1

Construction of Vectors and Transformation of *E. coli*

Strains and Vectors

The following *Escherichia coli* K12 strains were used: HB101 F$^-$, hsdS20(rB$^-$,mB$^-$) supE44, ara14, lambda$^-$, galK2, lacY1, proA2, rspL20, xyl-5, mtl-1, recA13, mcrA (+), mcrB(−) (Boyer et al. (1969) J. Mol. Biol. 41: 459–472); DH5alpha F$^-$, F80dlacZDM15, D(lacZYA-arqF)U169, recAI, endAI, gyrA, lambda$^-$, thi-I, hsdR17,(r$_k^-$,m$_k^+$), supE44, relAI, (BRL USA); RV308 DlacX74, galOP::IS2 (galOP308), strA, lambda$^-$ (Maurer et al. (1980) J. Mol. Biol. 139: 147–161), and BC50 xyl-7, ara-14, T4-R, lambda$^-$ (Kabi Pharmacia AB, Sweden). The strains HB101 and DH5alpha were used for subcloning of DNA fragments.

The plasmid pUC9 (Vieira et al. (1982) Gene 19: 259–268) was used for subcloning of an 847 bp Bam HI fragment of a cDNA copy of human Apo AI obtained from A. Sidoli, the University of Milano, Italy, and described in Sharp et al., Nucl. Acids Res. (1984) 12: 3917–3932. The nucleotide sequence of human Apo AI cDNA can be obtained from GenBank database under the accession number X02162 (Seilhammer et al. (1984) DNA 3: 309–317). This vector was designated pKP575. Also an 882 bp Eco RI - Pst I fragment of human Apo AI-M DNA (cDNA copy of Apo AI converted to Apo AI-M by site-directed mutagenesis, obtained from A. Sidoli, the University of Milano, Italy) was subcloned into the plasmid pUC9. This derivative was designated pKP576. The plasmids pKP683 and pKP764 as prepared below are derivatives of the plasmids pTrc 99 (described by Amann et al. (1988) Gene 69: 301–15; obtainable from Pharmacia P-L Biochemicals, Inc., Milwaukee, U.S.A.) and a pUC derivative with the transposon (Tn903) derived kanamycin resistance marker from pUC4-K (Vieira et al. (1982) Gene 19: 259–268, and Oka et al. (1981) J. Mol. Biol. 147: 217) and the transcription terminators (T1T2) of the bacteriophage fd, from pUEX2, (Bressan et al. (1987) Nucleic Acid. Res. 15: 10056).

Methods Employed

The bacterial strains were grown in Luria Bertani medium (LB) or yeast tryptone medium (2xYT) with ampicillin (Ap) 50 µg/ml or kanamycin (Km) 70 µg/ml for preparation of plasmid DNA and for small scale expression analysis (Sambrook et al. (1989) Cold Spring Harbor Laboratory Press). Tryptose blood agar base (Difco, USA), supplemented with Ap 50 µg/m or Km 70 µg/ml, were used for growing cells on agar plates. Recombinant DNA techniques were performed according to Sambrook et al. (1989) Cold Spring Harbor Laboratory Press. Restriction endonucleases and T4 DNA ligase were obtained from Boehringer Mannheim (Germany), New England Biolabs (Beverly, USA) and Pharmacia LKB Biotechnology AB (Uppsala, Sweden). Isopropyl-β-D-thiogalactoside (IPTG) was obtained from Sigma (St. Louis, USA). Low gelling and melting temperature agarose (NuSieve GTG, FMC Bioproducts, USA) was used to isolate DNA fragments. PCR amplifications were performed using the DNA thermal cycler and Taq DNA polymerase from Perkin-Elmer/Cetus Instruments (Norwalk, USA). Oligonucleotide linkers and primers were synthesized on a Pharmacia-LKB Gene Assembler Plus from Pharmacia LKB Biotechnology AB (Uppsala, Sweden) using the phosphite triester method on solid phase. The nucleotide sequence determination was performed on an Applied Biosystems 373A DNA sequencer, using the Taq DyeDeoxy™ Terminator Cycle Sequencing Kit from Applied Biosystems, Inc. (USA).

DNA Computer Programs Used

The Macintosh program PlasmidARTIST (version 1.2) (Clontech, USA) was used for drawing the plasmid maps and the GCG Sequence Analysis Software Package (Genetics Computer Group, Inc, Madison Wis. USA) was used for handling DNA sequences on Digital VAX computers.

Construction of Plasmid pKP683

Two oligonucleotides were synthesized (FIG. 1) SEQ ID No. 1 for fusing the Apo AI and Apo AI-M cDNA copies to DNA fragments encoding bacterial signal sequences. The 14 bp Eco RI and Nco I fragment and the 40 bp Nco I fragment of pKP575 were replaced by a synthetic 37 bp Eco RI - Nco I fragment (FIG. 1) SEQ ID No. 1 into a plasmid designated pKP580. The Bbs I cleavage site in this synthetic DNA fragment gives the same cleavage site as Mlu I, which facilitates cloning of different fragments encoding bacterial signal sequences. The plasmid pKP631 was constructed by replacing a 702 bp Nco I - Dra III fragment of pKP575 (Apo AI) by a 702 bp Nco I - Dra III fragment of pKP576 (Apo AI-M). From the plasmid pKP631 a 846 bp Bbs I - Hind III fragment was isolated and inserted at the MIU I and Hind III of a plasmid vector that was designated pKP682. This vector contains a tac promoter (Ptac), a derivative of an ompA signal sequence, two transcription terminators and a kanamycin resistance marker. A 1541 bp Nru I - Nru I fragment was isolated from pKP682 and was inserted into a similar vector but with the Ptac replaced by the Ptrc promoter. This expression vector was designated pKP683 (FIG. 5).

Construction of Plasmid pKP764

Figure 6:
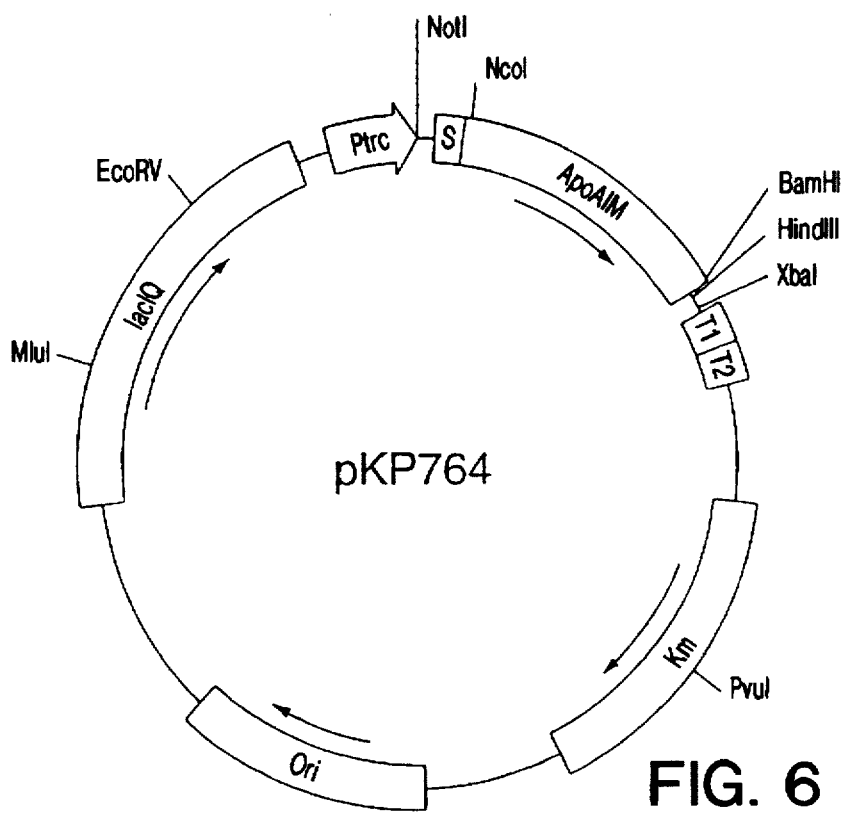
FIG. 6 shows the expression vector pKP764. The important structural and regulatory elements are outlined as boxes with arrows indicating the direction of translation and replication respectively. Some of the unique restriction enzyme sites are indicated outside the plasmid circle. The abbreviations used for FIG. 6 are the same as used for FIG. 5.

The plasmid pKP764 (FIG. 6) was constructed by replacing the 115 bp Dra III - Hind III fragment of the plasmid pKP683 prepared above by a 14 bp synthetic DNA fragment (FIG. 2) SEQ ID No. 3, containing stronger translation terminators SEQ ID No. 4 and destroying the Dra III site by the introduction of an A at the end of the Dra III overhanging 3' end (indicated by Dra IIID in FIG. 2) SEQ ID No. 3.

Transformation of *E. coli* Strains with Plasmids pKP683 and pKP764

Plasmids pKP683 and pKP764 as prepared above were used to transform *E. coli* strains RV308 and BC50 as described in Sambrook et al. (1989) Cold Spring Harbor Laboratory Press. The obtained *E. coli* strains RV308/pKP683 and RV308/pKP764 to be used for growth in bioreactors were prepared as follows. Cells were grown overnight in LB or 2xYT supplemented with Km in shaker flasks at 30° C. After centrifugation, the cells were resuspended in ½ volume of deep freeze storage medium according to Gergen et al. (1979) Nucleic Acids Res. 7: 2115. Aliquots were dispensed into 1 ml cryovials and stored at −75° C. until used.

Analysis of Plasmids

The plasmid constructions used for expression experiments and for production of Apo AI-M were analysed using restriction enzyme mapping, and the structural gene of Apo SEQ ID No. 5 was confirmed by nucleotide sequence determination.

Small Scale Production of Apo AI-M

For small scale expression of Apo AI-M, 20 ml of LB or 2xYT supplemented with Km were inoculated with the *E. coli* strains RV308/pKP683 or RV308/pKP764 in a 250 ml shaker flask. The cells were grown at 30° C. overnight with vigorous shaking. These cells were diluted 1/100 into fresh medium (20 ml) and were grown at 37° C. to an optical density at 600 nm (OD) of about 1, when IPTG was added to a final concentration of 0.5 or 1 mM. The cells were incubated for an additional 90 minutes or overnight. The cells were separated from the growth medium by centrifugation and the medium was analysed for the production of Apo AI-M. Aliquots of the medium were passed through a filter device, the nitrocellulose filter was removed and the amount of Apo AI-M was determined using anti-Apo AI antibodies. Also the Apo AI-M produced from different constructions was determined by SDS polyacrylamide gel electrophoresis (SDS-PAGE) and western blotting analysis, using proteins obtained from whole cells and medium.

EXAMPLE 2

Production of Apo AI-M in a Bioreactor

Growth Media for Cells Grown in Bioreactors

Medium A: 16 g/l tryprone (Difco, USA), 8 g/l yeast extract (Difco, USA), 5 g/l NaCl, and 0.05 g/l kanamycin.

Medium B: 2.5 g/l $(NH_4)_2SO_4$, 3 g/l $KH_2PO_4$, 2 g/l $K_2HPO_4$, 0.5 g/l $Na_3$-citrate, 5 g/l yeast extract (Difco, USA). After sterilization, the medium was supplemented with: 10 g/l initial glucose, 0.05 g/l kanamycin, 1 g/l $MgSO_4 \times 7\ H_2O$ and 0.07 g/l thiamine hydrochloride. A trace element solution (1 ml/l) and a vitamin solution (0.65 ml/l) were added. The trace element solution contained: 27 g/l $FeCl_3 \times 6\ H_2O$, 4 g/l $ZnSO_4 \times 7\ H_2O$, 7 g/l $CoCl_2 \times 6\ H_2O$, 7 g/l $Na_2MoO_4 \times 2\ H_2O$, 8 g/l $CuSO_4 \times 5\ H_2O$, 2 g/l $H_3BO_3$, 5 g/l $MnSO_4 \times 4\ H_2O$, 11 g/l $CaCl_2 \times 2\ H_2O$ and 50 ml/l HCl. The vitamin solution contained: 0.5 g/l calcium pantothenate, 0.5 g/l choline chloride, 0.5 g/l folic acid, 1 g/l inositol, 0.5 g/l nicotinamide, 0.5 g/l pyridoxine hydrochloride, 0.05 g/l riboflavin and 0.5 g/l thiamine hydrochloride. Adecanol (0.2 ml/l) was used as anti-foam. When necessary, further additions of anti-foam was made during the cultivation.

Analysis of Apo AI-M in Fermentation Media

Samples of fermentation media were centrifuged and the concentration of Apo AI-M in the supernatant was determined by radioimmunoasssay (Apolipoprotein AI RIA 100 kit, Art. No. 109152-01, Kabi Pharmacia AB, Sweden).

Cultivation of RV308/pKP683 in a Bioreactor of 3.5 Liters

Deep frozen stock culture was used to inoculate 500 ml of medium A and precultivated in 2 liters baffled Erlenmeyer flasks at 30° C. for 8–10 hrs. An inoculum volume corresponding to 10% of the bioreactor working volume was transferred to the bioreactor.

The cultivation was performed in a bioreactor of 3.5 liters (Belach AB, Sweden) with a working volume of 2.5 liters. The temperature was 30° C. during the growth phase before induction and then raised to 37° C. The pH was maintained at 7.0 with a solution of 25% ammonia. The aeration rate was held at 1 vvm and the dissolved oxygen tension (D.O.T.) was kept at 30% by adjusting the impeller speed. After the initial glucose was consumed, a glucose fed-batch was initiated, keeping the system at glucose limitation by feeding a 60% solution of glucose. The initial feed rate, 0.04 g/min was kept for 3 hrs and then gradually increased to 0.4 g/min during 3 hrs. Cell growth was monitored by following the optical density at 600 nm.

Figure 7:
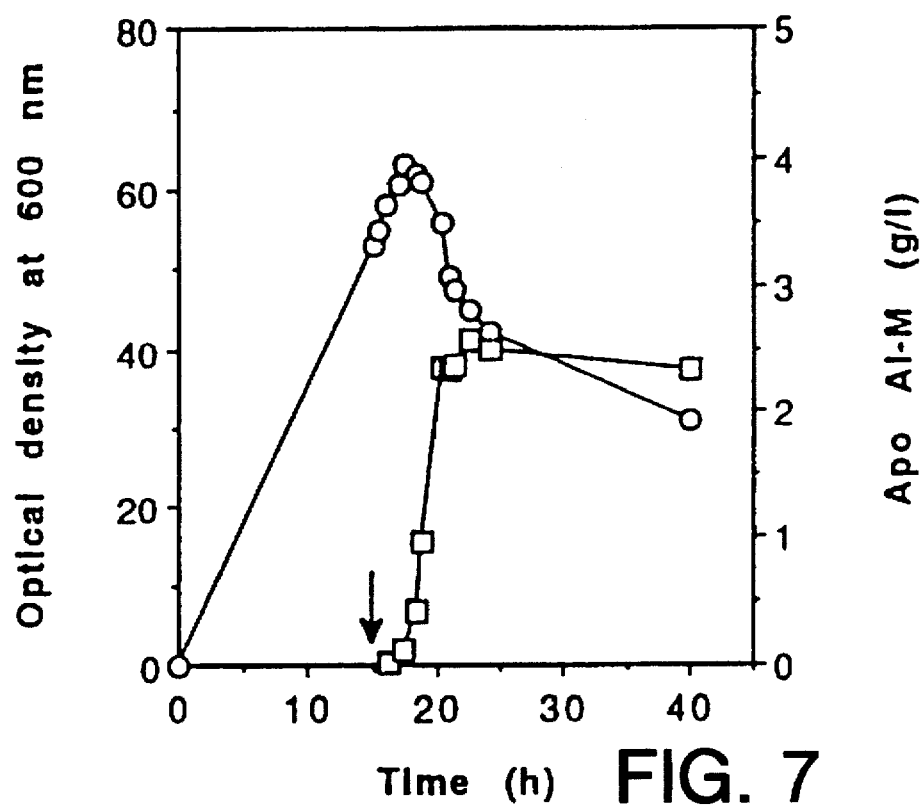
FIG. 7 shows production of Apo AI-M in a bioreactor of 3.5 liters, using *E. coli* strain RV308/pKP683. Symbols: (open circle), optical density at 600 nm; (open box), Apo AI-M concentration (g/l growth medium). Time of induction (by supplementation of IPTG) is indicated by an arrow.

After 16 hrs of cultivation, at an OD of 58, protein synthesis was induced by adding 0.5 mM IPTG and the temperature was increased to 37° C. Four hours after the induction the concentration of Apo AI-M was 2.3 g/l, and after additional 2 hrs the concentration was 2.5 g/l. The results are shown in FIG. 7.

EXAMPLE 3

Cultivation of RV308/pKP764 in a Bioreactor of 3.5 Liters

Figure 8:
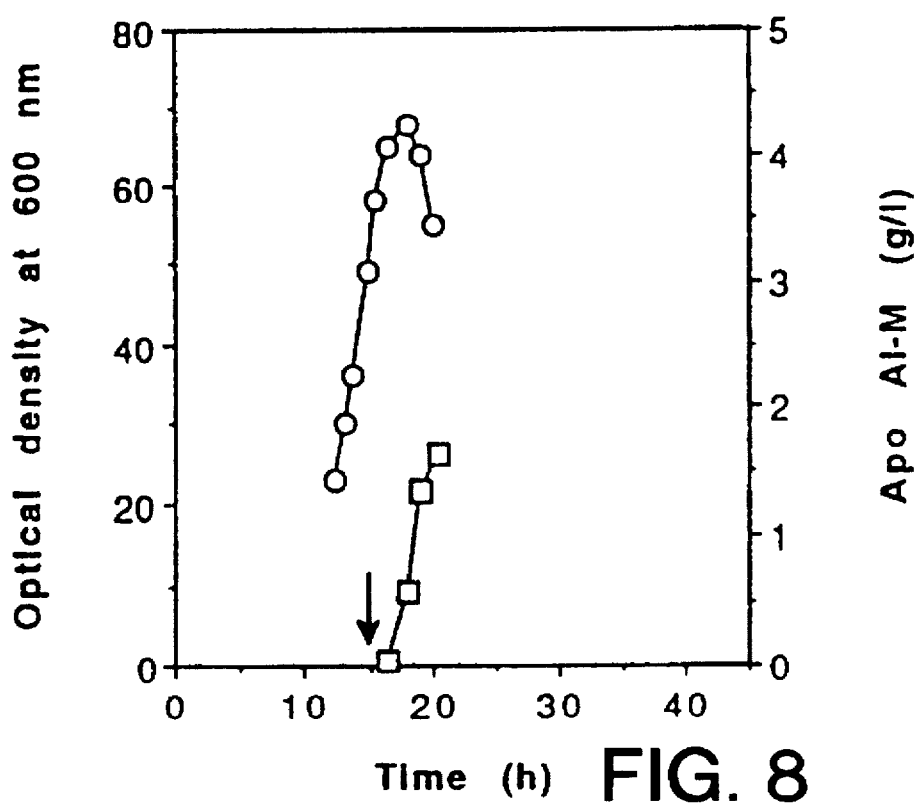
FIG. 8 shows production of Apo AI-M in a bioreactor of 3.5 liters using *E. coli* strain RV308/pKP764. Symbols are as in FIG. 7.

Medium and growth conditions were the same as described in Example 2. At an OD of 58, after 15.5 hrs of cultivation, IPTG was added and the temperature was raised. Five hours later the concentration of Apo AI-M in the supernatant was 1.6 g/l. The results are shown in FIG. 8.

EXAMPLE 4

Cultivation of BC50/pKP683 in a Bioreactor of 3.5 Liters

Figure 9:
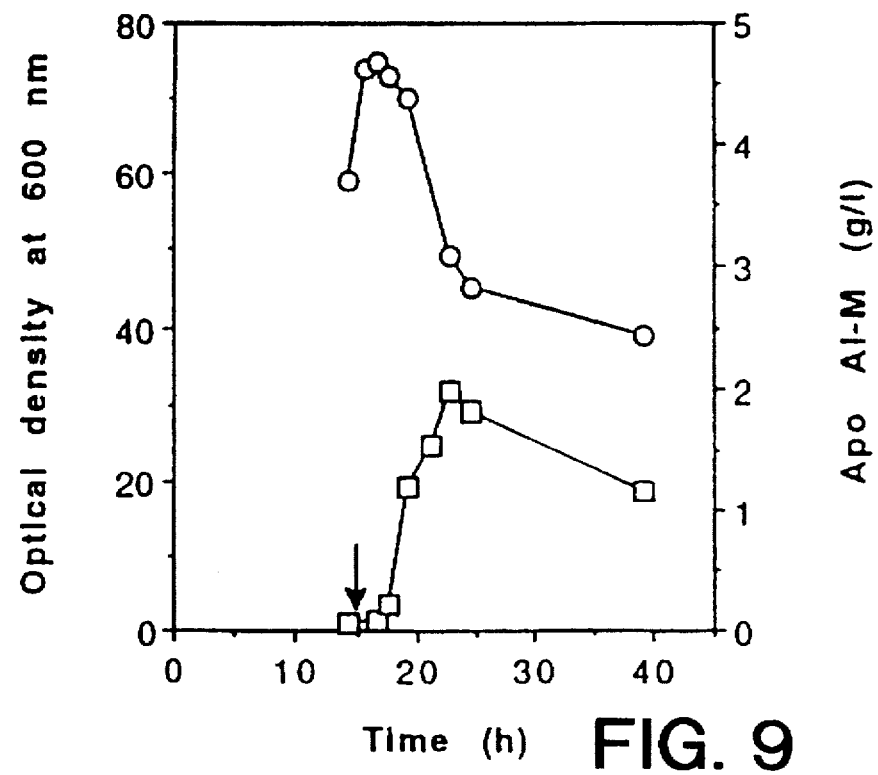
FIG. 9 shows production of Apo AI-M in a bioreactor of 3.5 liters, using *E. coli* strain BC50/pKP683. Symbols are as in FIG. 7.

The fermentation was performed according to example 2, with the exception that the 1.0 mM IPTG was used for induction. After 15 hrs. at an OD of 74, IPTG was added and the temperature was raised. 7.5 hrs after induction the supernatant concentration of Apo AI-M was 2.0 g/l. The results are shown in FIG. 9.

EXAMPLE 5

Cultivation of BC50/pKP764 in a Bioreactor of 3.5 Liters

Figure 10:
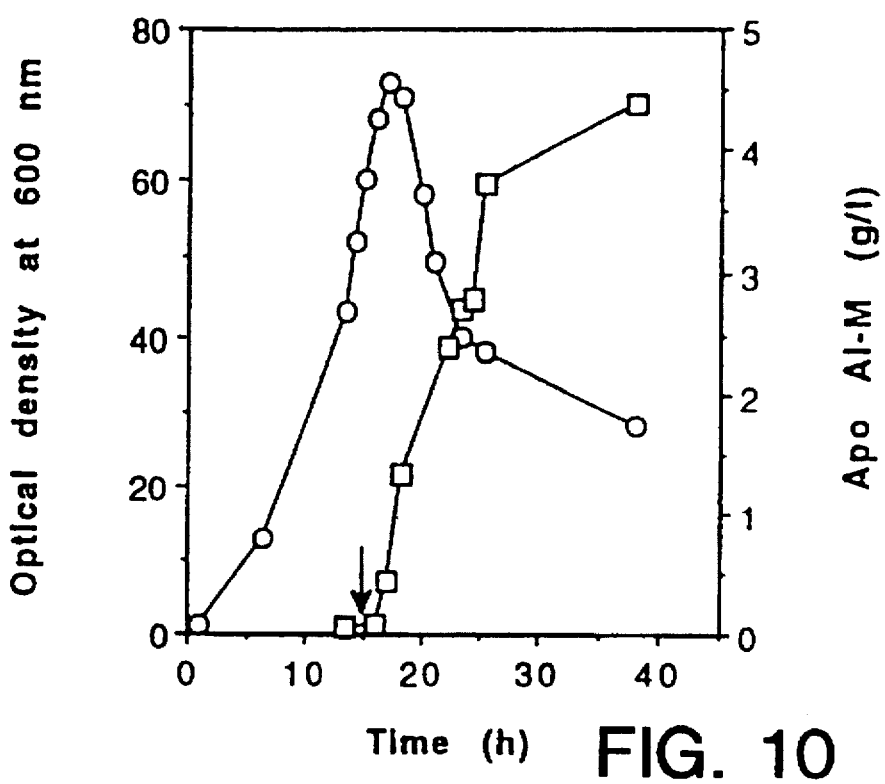
FIG. 10 shows production of Apo AI-M in a bioreactor of 3.5 liters, using *E. coli* strain BC50/pKP764. Symbols are as in FIG. 7.

The cultivation was carried out as described in Example 2, except that no kanamycin was added to the bioreactor medium. After 15 hrs, at an OD of 60, IPTG was added and the temperature was raised. 10 hrs later the concentration of Apo AI-M in the supernatant was 3.7 g/l and 22 hrs after induction, the concentration was 4.4 g/l. The results are shown in FIG. 10.

EXAMPLE 6

Cultivation of BC50/pKP764 in a Bioreactor of 75 Liters

Figure 11:
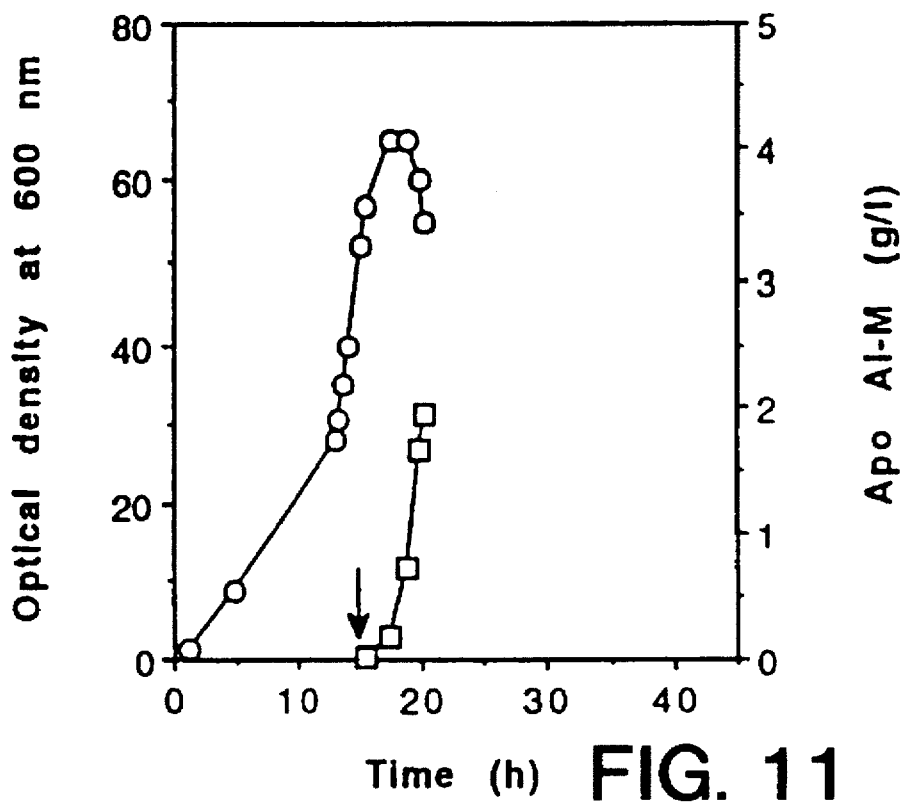
FIG. 11 shows production of Apo AI-M in a bioreactor of 75 liters, using *E. coli* strain BC50/pKP764. Symbols are as in FIG. 7.

The cultivation was performed in a bioreactor of 75 liters (Chemap AG, Switzerland) with a working volume of 35 liters. Media and growth conditions were the same as in Example 2. To keep the D.O.T. value above 30%, the air pressure was raised to 1.4 bar for 2 hrs following the induction. IPTG was added and the temperature was raised after 16 hrs of fermentation at an OD of 57. The concentration of Apo AI-M was 1.9 g/l, 4.5 hrs after the time of induction. The results are shown in FIG. 11.

EXAMPLE 7

Cultivation of BC50/pKP764 in a Bioreactor of 300 Liters

Figure 12:
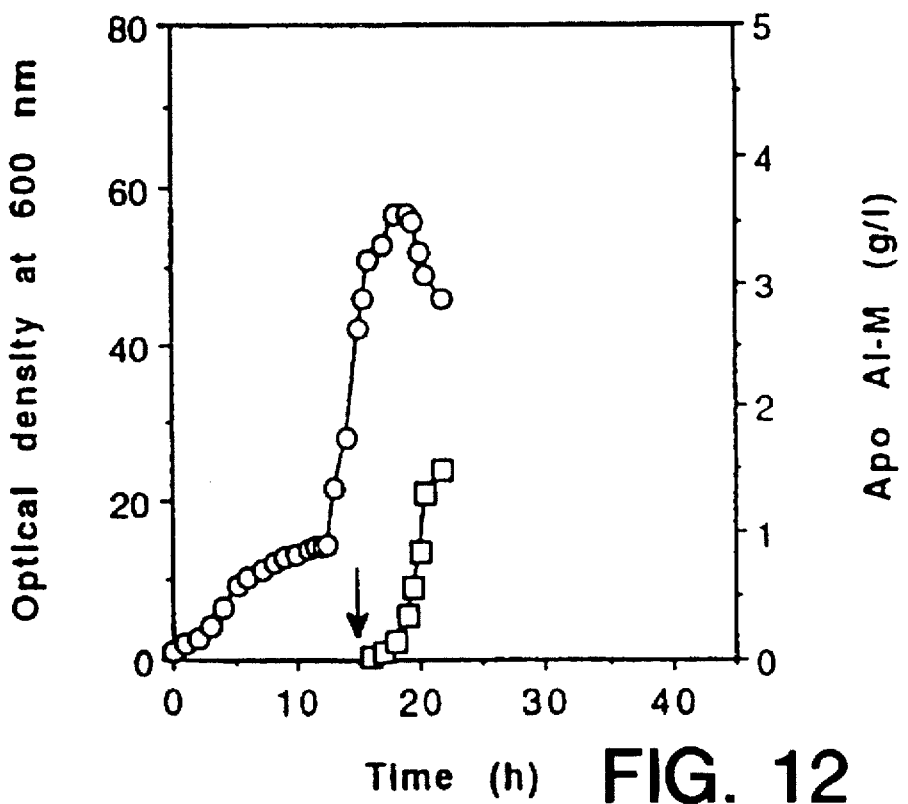
FIG. 12 shows production of Apo AI-M in a bioreactor of 300 liters, using *E. coli* strain BC50/pKP764. Symbols are as in FIG. 7.

A bioreactor of 300 liters (Chemoferm AB, Sweden) with a working volume of 180 liters was used. The inoculum was prepared as described in Example 2, except that the precultivation time in shake flasks was 14 hrs. The inoculum was transferred to a 50 liters seed bioreactor with a working volume of 18 liters. The medium used in the shake flasks as well as in the bioreactor was medium A. The seed bioreactor medium was supplemented with 5 g/l of glucose and the temperature was 30° C. The pH and aeration were as in Example 2 and the D.O.T. was never below 30%. When the culture reached an OD of 4, the content of the seed bioreactor was transferred to the bioreactor of 300 liters. In this bioreactor the temperature, pH and aeration of the medium were as described in Example 2. Before induction the D.O.T. was kept at or above 30% by increasing the impeller speed up to its maximum and thereafter increasing the air pressure. After induction the air pressure was increased to 2 bars resulting in a D.O.T. of 15–20%. After 16 hrs of cultivation in the bioreactor when the culture had an OD of 51, IPTG was added and the temperature was increased to 37° C. The concentration of Apo AI-M was 1.3 g/l, 5 hrs after induction and during the following hour, while the bioreactor was cooled, the concentration of Apo AI-M increased to 1.5 g/l. The results are shown in FIG. 12.

EXAMPLE 8

Cultivation of BC50/pKP764 in a Bioreactor of 3.5 Liters

Figure 13:
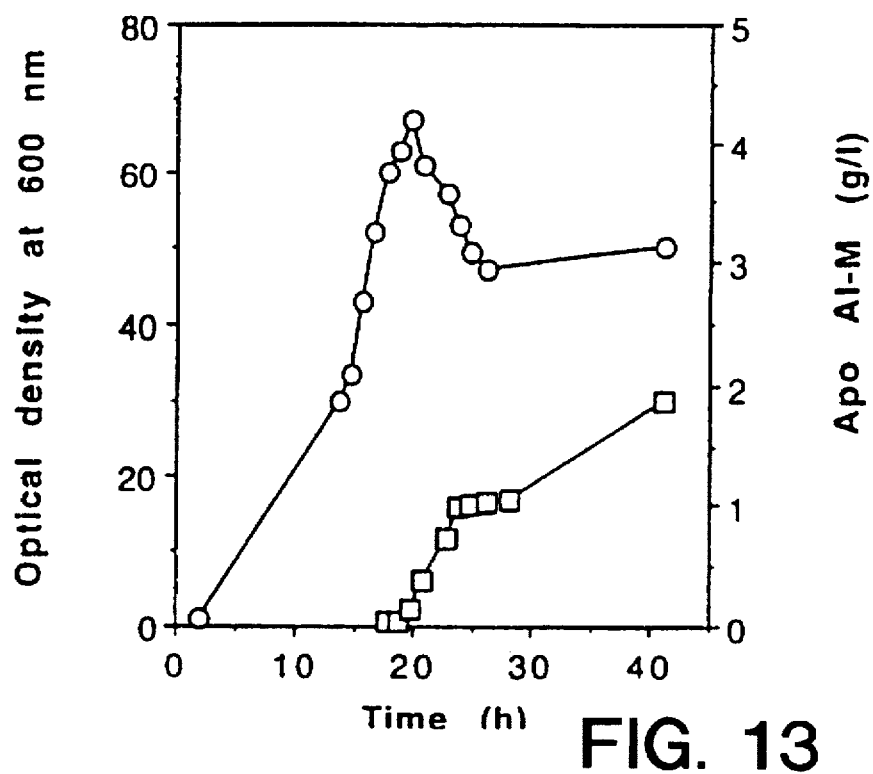
FIG. 13 shows production of Apo AI-M in a bioreactor of 3.5 liters, using *E. coli* strain BC50/pKP764. Symbols are as in FIG. 7.

The cultivation was carried out as described in Example 2 with the following exceptions: The initial amount of glucose (15 g/l) was consumed after 12 hours. Thereafter a 60% solution of glucose was added, using a preprogrammed feed profile, changing the feed rate linearly over the specified time intervals. The D.O.T. was kept constant at 30%, controlled by the agitator speed. The feed was started at a flow of 0.09 ml/min and then increased to 0.72 ml/min during 4 hours, whereafter it was constant for 48 minutes. Thereafter it was decreased to 0.57 ml/min during 1 hour and 36 minutes, then decreased to 0.32 ml/min during 1 hour and 48 minutes and then to 0.22 ml/min during 54 minutes. The feed was finally decreased to 0.18 ml/min during 5 hours and 54 minutes and then kept constant until the end of fermentation at 41 hours. After 18 hours, at an OD of 61, IPTG was added and the temperature was raised. The supernatant concentration of Apo AI-M, 23 hours after induction, was 1.9 g/l. The results are shown in FIG. 13.

EXAMPLE 9

Cultivation of RV308/pKP683 in a Bioreactor of 3.5 Liters

Figure 14:
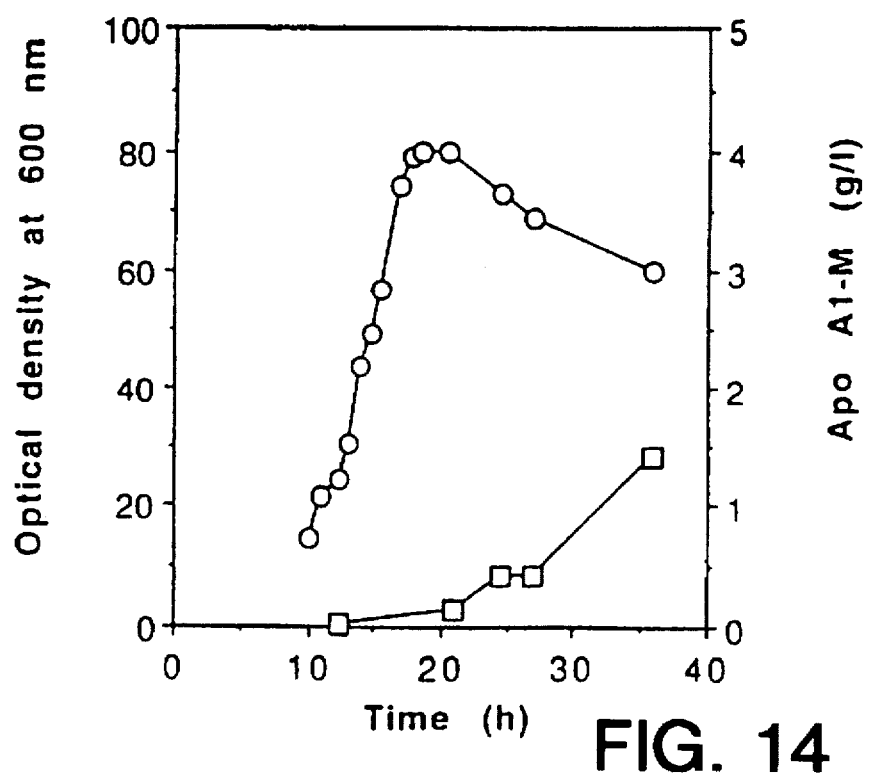
FIG. 14 shows production of Apo AI-M in a bioreactor of 3.5 liters, using *E. coli* strain RV308/pKP683. Symbols are as in FIG. 7.

The cultivation was carried out as described in Example 2 with the exception that the fermentation was performed at a constant temperature, 30° C. After 18 hours, at an OD of 80, IPTG was added. 17.5 hours after induction, the supernatant concentration of Apo AI-M was 1.4 g/l. The results are shown in FIG. 14.

EXAMPLE 10

Characterization of Intact Recombinant Apo AI-M

Apo AI-M was produced by in E. coli as described in Example 6 and thereafter purified by standard chromatographic methods. The product was compared to the deduced amino acid sequence shown in FIG. 4 SEQ ID No. 6.

N-terminal Sequence Determination

The N-terminal sequence of the intact protein was determined by Edman degradation (20 cycles) using a Milligen Biosearch Prosequencer type 6000. The sequence found was identical to the N-terminal of Apo AI-M.

C-terminal Residue Determination

Recombinant Apo AI-M was digested with carboxypeptidase P (Boehringer Mannheim) whereafter the released amino acids were analysed using the Picotag™ method (Waters). The C-terminal residue was unequivocally identified as glutamine.

Amino Acid Composition

The amino acid composition of the intact protein was determined using a Beckman 6300 amino acid analyzer after acid hydrolysis. The results are shown in Table 1 below. The composition found was consistent with that of Apo AI-SEQ ID No. 6.

TABLE 1

| Amino acid | Expected | Found |
|---|---|---|
| Asx | 21 | 20.8 |
| Thr | 10 | 9.2 |
| Ser | 15 | 13.9 |
| Glx | 46 | 47.0 |
| Gly | 10 | 10.4 |
| Ala | 19 | 19.3 |
| Cys | 1 | n.d.[1] |
| Val | 13 | 11.4 |
| Met | 3 | n.d. |
| Ile | 0 | 0.0 |
| Leu | 37 | 36.8 |
| Tyr | 7 | 6.6 |
| Phe | 6 | 5.8 |
| His | 5 | 4.9 |
| Lys | 21 | 20.2 |
| Arg | 15 | 14.8 |
| Pro | 10 | 10.6 |
| Trp | 4 | n.d. |

[1]n.d. = not determined

Circular Dichroic (CD) Spectrum

Figure 15:
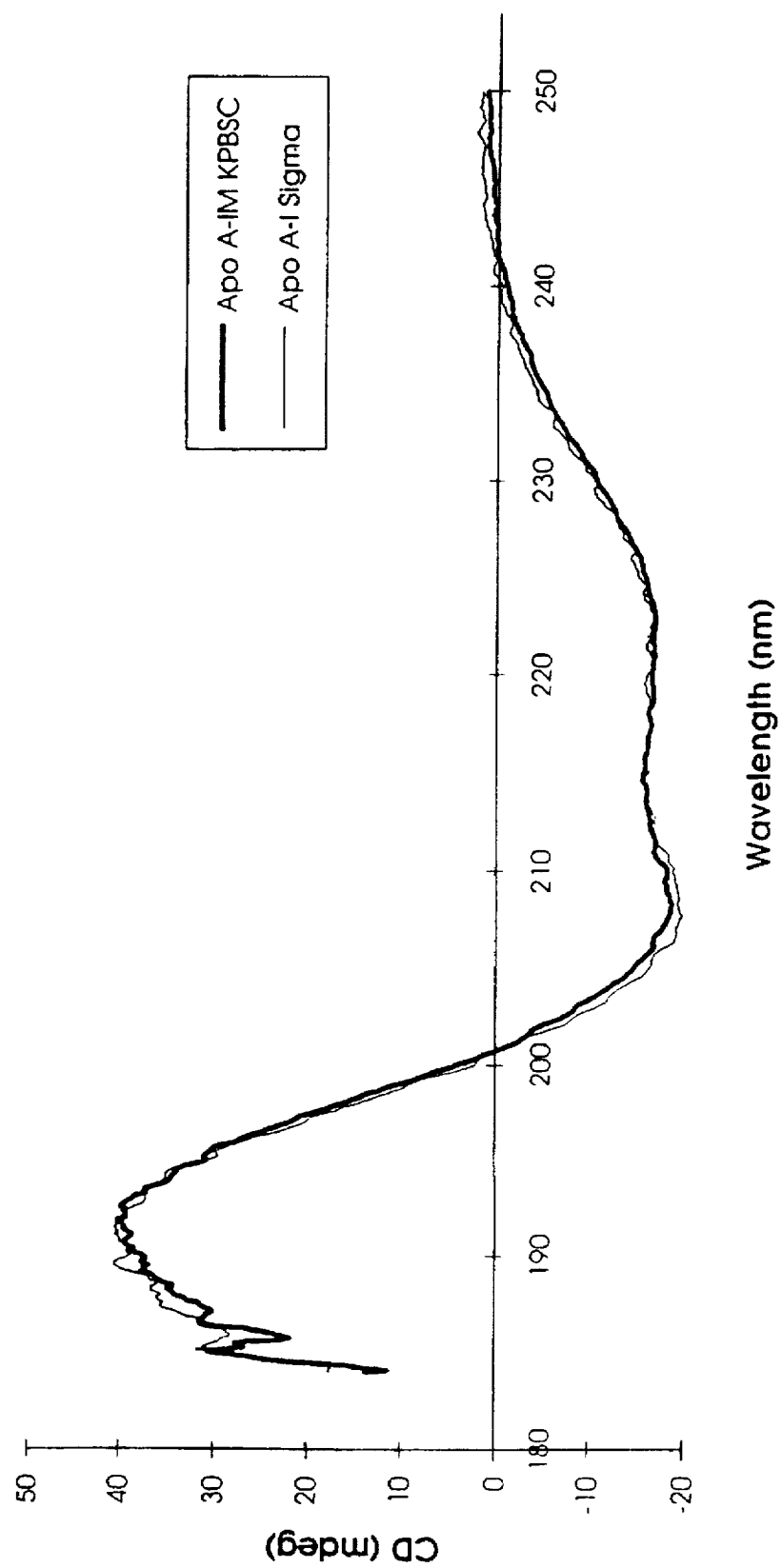
FIG. 15 shows circular dichroic spectra of recombinant Apo AI-M (bold line) and human Apo AI (thin line).

The CD spectra of the intact recombinant protein and of human Apo-A1 standard (Sigma) were recorded in 20 mM sodium phosphate buffer, pH 7.5. The observed differences were within experimental error (FIG. 15).

EXAMPLE 11

Characterisation of a C-terminal Fragment

A 59-residue C-terminal fragment (residues 185–243) was prepared by cleavage with hydroxylamine. Recombinant Apo AI-M (480 μg) was dissolved in 0.5 ml cleavage solution, containing 2M hydroxylamine, 3M guanidinium chloride, 0.2M NaOH and 2 mM EDTA. The initial pH of the cleavage solution was 9.4. The reaction mixture was incubated for 5 hrs at 40° C. The C-terminal fragment was purified by reverse phase HPLC, using a YMC-pack protein RP column (YMC Co., Inc., Japan), eluted with a gradient of 10–60% acetonitrile in water, containing 0.25% pentafluoropropionic acid. The C-terminal fragment eluted as a single, non-fluorescent, sharp peak at 36–38% acetonitrile.

N-terminal Sequence

The sequence of the entire C-terminal fragment was determined by Edman degradation as described in Example 8. The sequence found was identical to Apo AI-M, residues 185–243.

C-terminal Residue

The C-terminal residue of the C-terminal fragment was unequivocally identified as glutamine as described in Example 10.

Amino Acid Composition

The amino acid composition of the C-terminal fragment was determined as described in Example 10, and the results are shown in Table 2 below. The composition found was consistent with that of Apo AI-M, residues 185–243.

TABLE 2

| Amino acid | Expected | Found |
|---|---|---|
| Asx | 2 | 2.6 |
| Thr | 4 | 3.6 |
| Ser | 5 | 5.0 |

TABLE 2-continued

| Amino acid | Expected | Found |
|---|---|---|
| Glx | 9 | 9.7 |
| Gly | 3 | 3.7 |
| Ala | 7 | 6.8 |
| Cys | 0 | n.d.[1] |
| Val | 2 | 1.9 |
| Met | 0 | n.d. |
| Ile | 0 | 0.0 |
| Leu | 11 | 10.6 |
| Tyr | 2 | 2.0 |
| Phe | 2 | 2.1 |
| His | 2 | 1.8 |
| Lys | 6 | 5.6 |
| Arg | 2 | 2.1 |
| Pro | 2 | 2.2 |
| Trp | 0 | n.d. |

[1] n.d. = not determined

We claim:

1. An expression vector giving extracellular production of apolipoprotein AI-M (Milano) SEQ ID No. 6 using *E. coli*, comprising a plasmid carrying an origin of replication, an inducible promoter sequence selected from the group consisting of the lac promoter, the trp promoter, hybrids between the lac promoter and the trp promoter, and a DNA sequence SEQ ID Nos. 5 and 7 coding for a signal peptide, a DNA sequence coding for apolipoprotein AI-M SEQ ID No. 6, and a transcription terminator.

2. The expression vector according to claim 1, characterized in that said DNA sequence SEQ ID Nos. 5 and 7 coding for apolipoprotein AI-M SEQ ID No. 6 is a sequence coding for the mature protein.

3. The expression vector according to claim 1 characterized in that said inducible promoter is a trc promoter or a functional derivative thereof.

4. The expression vector according to claim 1 characterized in that said signal sequence SEQ ID Nos. 5 and 7 is a derivative of the ompA signal sequence.

5. An *E. coli* strain transformed with the expression vector according to claim 1.

6. A method of producing apolipoprotein AI-M (Milano) SEQ ID No. 6, characterized in that it comprises the steps of:
   cultivating a transformed *E. coli* strain according to claim 5 in a growth medium,
   inducing expression of the apolipoprotein AI-M protein SEQ ID No. 6 in the logarithmic growth phase before the stationary phase is attained, and
   separating the product from the growth medium.

7. The method according to claim 6, characterized in that the cultivation is started at a low temperature, and that the temperature is raised in the logarithmic growth phase before, simultaneously with or after the induction.

8. The method according to claim 7, characterized in that the cultivation is started at from about 29° to about 31° C., preferably at about 30° C., and that the temperature is raised in the logarithmic growth phase to about 37° C.

9. The method according to claim 6, characterized in that the cultivation is performed at a constant temperature, preferably from about 25° to about 37° C.

10. The method according to claim 6 characterized in that induction is performed when the growth medium has reached an optical density of at least about 50.

11. The method according to claim 6 characterized in that harvest is performed at the optimum cell culture state.

12. The method according to claim 6 characterized in that the growth medium comprises yeast extract, optionally supplemented with tryptone.

13. The method according to claim 6 characterized in that the production medium is free from antibiotics.

14. The expression vector according to claim 2, characterized in that said inducible promoter is a trc promoter or a functional derivative thereof.

15. The expression vector according to claim 2, characterized in that said signal sequence is a derivative of the ompA signal sequence.

16. The expression vector according to claim 3, characterized in that said signal sequence is a derivative of the ompA signal sequence.

17. An *E. coli* strain transformed with the expression vector according to claim 2.

18. An *E. coli* strain transformed with the expression vector according to claim 3.

19. An *E. coli* strain transformed with the expression vector according to claim 4.

20. The method according to claim 7 characterized in that induction is performed when the growth medium has reached an optical density of at least about 50.

21. The expression vector according to claim 1, wherein said hybrid between the lac promoter and the trp promoter is the tac promoter.

22. The expression vector according to claim 1, wherein said expression vector provides extracellular production of apolipoprotein AI-M (Milano) SEQ ID No. 6 using an *E. coli* strain selected from the group consisting of RV308 and BC50.

23. The expression vector according to claim 1, wherein said plasmid is selected from the group consisting of pKP576, pKP631, pKP764, pKP682, and pKP683.

24. An *E. coli* strain according to claim 5, wherein said *E. coli* strain is selected from the group consisting of RV308 and BC50.

25. The method according to claim 6, wherein said *E. coli* strain is selected from the group consisting of RV308 and BC50.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
      ( A ) LENGTH: 41 base pairs
      ( B ) TYPE: nucleic acid
      ( C ) STRANDEDNESS: both
      ( D ) TOPOLOGY: linear ( i i ) MOLECULE TYPE: other nucleic acid
      ( A ) DESCRIPTION: /desc = "synthetic"

( i x ) FEATURE:
      ( A ) NAME/KEY: misc_feature
      ( B ) LOCATION: 1..5
      ( D ) OTHER INFORMATION: /label=Eco-RI ( i x ) FEATURE:
      ( A ) NAME/KEY: misc_feature
      ( B ) LOCATION: 15..18
      ( D ) OTHER INFORMATION: /label=Bbs-I ( i x ) FEATURE:
      ( A ) NAME/KEY: misc_feature
      ( B ) LOCATION: 37..41
      ( D ) OTHER INFORMATION: /label=Nco-I ( i x ) FEATURE:
      ( A ) NAME/KEY: CDS
      ( B ) LOCATION: 1..39

( x i ) SEQUENCE DESCRIPTION: SEQ ID NO:1:

```
AAT TCA GAA GAC ACC GCG GAC GAG CCA CCG CAG AGC CCA TG                    41
Asn Ser Glu Asp Thr Ala Asp Glu Pro Pro Gln Ser Pro
 1           5               10
```

(2) INFORMATION FOR SEQ ID NO:2:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:2:

```
Asn Ser Glu Asp Thr Ala Asp Glu Pro Pro Gln Ser Pro
 1           5               10
```

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "synthetic"

(ix) FEATURE:
        (A) NAME/KEY: misc_feature
        (B) LOCATION: 1..6
        (D) OTHER INFORMATION: /label=Dra-III (ix) FEATURE:
        (A) NAME/KEY: misc_feature
        (B) LOCATION: 17..21
        (D) OTHER INFORMATION: /label=Hind-III (ix) FEATURE:
        (A) NAME/KEY: CDS
        (B) LOCATION: 2..10

(xi) SEQUENCE DESCRIPTION: SEQ ID NO:3:

```
C CAG TAA TAA GGATCCAAGC T                                                21
  Gln  *   *
       15
```

(2) INFORMATION FOR SEQ ID NO:4:

(i) SEQUENCE CHARACTERISTICS:
        (A) LENGTH: 1 amino acid
        (B) TYPE: amino acid
        (D) TOPOLOGY: linear (ii) MOLECULE TYPE: peptide (xi) SEQUENCE DESCRIPTION: SEQ ID NO:4:

```
Gln
 1
```

(2) INFORMATION FOR SEQ ID NO:5:

(i) SEQUENCE CHARACTERISTICS:
        (A) LENGTH: 964 base pairs
        (B) TYPE: nucleic acid
        (C) STRANDEDNESS: both
        (D) TOPOLOGY: both (ii) MOLECULE TYPE: cDNA to mRNA (ix) FEATURE:
        (A) NAME/KEY: mat_peptide (B) LOCATION: 117..847

(ix) FEATURE:
(A) NAME/KEY: sig_peptide
(B) LOCATION: 54..116

(ix) FEATURE:
(A) NAME/KEY: CDS
(B) LOCATION: 54..847

(xi) SEQUENCE DESCRIPTION: SEQ ID NO:5:

| | | | | | |
|---|---|---|---|---|---|
| GCGGCCGCGG CTAATTGACA TGGCGTATTT TGGATGATAA CGAGGCGCAA AAA ATG | | | | | 56 |
| | | | | Met | |
| | | | | -21 | |

| AAA | AAG | ACA | GCT | ATC | GCG | ATT | GCA | GTG | GCA | CTG | GCT | GGT | TTC | GCT | ACC | 104 |
|---|---|---|---|---|---|---|---|---|---|---|---|---|---|---|---|---|
| Lys | Lys | Thr | Ala | Ile | Ala | Ile | Ala | Val | Ala | Leu | Ala | Gly | Phe | Ala | Thr | |
| -20 | | | | -15 | | | | | -10 | | | | | | -5 | |

| GTA | GCG | AAC | GCG | GAC | GAG | CCA | CCG | CAG | AGC | CCA | TGG | GAT | CGA | GTG | AAG | 152 |
|---|---|---|---|---|---|---|---|---|---|---|---|---|---|---|---|---|
| Val | Ala | Asn | Ala | Asp | Glu | Pro | Pro | Gln | Ser | Pro | Trp | Asp | Arg | Val | Lys | |
| | | | | 1 | | | | 5 | | | | | | 10 | | |

| GAC | CTG | GCC | ACT | GTG | TAC | GTG | GAT | GTG | CTC | AAA | GAC | AGC | GGC | AGA | GAC | 200 |
|---|---|---|---|---|---|---|---|---|---|---|---|---|---|---|---|---|
| Asp | Leu | Ala | Thr | Val | Tyr | Val | Asp | Val | Leu | Lys | Asp | Ser | Gly | Arg | Asp | |
| | | 15 | | | | 20 | | | | | 25 | | | | | |

| TAT | GTG | TCC | CAG | TTT | GAA | GGC | TCC | GCC | TTG | GGA | AAA | CAG | CTA | AAC | CTA | 248 |
|---|---|---|---|---|---|---|---|---|---|---|---|---|---|---|---|---|
| Tyr | Val | Ser | Gln | Phe | Glu | Gly | Ser | Ala | Leu | Gly | Lys | Gln | Leu | Asn | Leu | |
| | 30 | | | | | 35 | | | | | 40 | | | | | |

| AAG | CTC | CTT | GAC | AAC | TGG | GAC | AGC | GTG | ACC | TCC | ACC | TTC | AGC | AAG | CTG | 296 |
|---|---|---|---|---|---|---|---|---|---|---|---|---|---|---|---|---|
| Lys | Leu | Leu | Asp | Asn | Trp | Asp | Ser | Val | Thr | Ser | Thr | Phe | Ser | Lys | Leu | |
| 45 | | | | | 50 | | | | | 55 | | | | | 60 | |

| CGC | GAA | CAG | CTC | GGC | CCT | GTG | ACC | CAG | GAG | TTC | TGG | GAT | AAC | CTG | GAA | 344 |
|---|---|---|---|---|---|---|---|---|---|---|---|---|---|---|---|---|
| Arg | Glu | Gln | Leu | Gly | Pro | Val | Thr | Gln | Glu | Phe | Trp | Asp | Asn | Leu | Glu | |
| | | | | 65 | | | | | 70 | | | | | 75 | | |

| AAG | GAG | ACA | GAG | GGC | CTG | AGG | CAG | GAG | ATG | AGC | AAG | GAT | CTG | GAG | GAG | 392 |
|---|---|---|---|---|---|---|---|---|---|---|---|---|---|---|---|---|
| Lys | Glu | Thr | Glu | Gly | Leu | Arg | Gln | Glu | Met | Ser | Lys | Asp | Leu | Glu | Glu | |
| | | | 80 | | | | | 85 | | | | | 90 | | | |

| GTG | AAG | GCC | AAG | GTG | CAG | CCC | TAC | CTG | GAC | GAC | TTC | CAG | AAG | AAG | TGG | 440 |
|---|---|---|---|---|---|---|---|---|---|---|---|---|---|---|---|---|
| Val | Lys | Ala | Lys | Val | Gln | Pro | Tyr | Leu | Asp | Asp | Phe | Gln | Lys | Lys | Trp | |
| | | 95 | | | | | 100 | | | | | 105 | | | | |

| CAG | GAG | GAG | ATG | GAG | CTC | TAC | CGC | CAG | AAG | GTG | GAG | CCG | CTG | CGC | GCA | 488 |
|---|---|---|---|---|---|---|---|---|---|---|---|---|---|---|---|---|
| Gln | Glu | Glu | Met | Glu | Leu | Tyr | Arg | Gln | Lys | Val | Glu | Pro | Leu | Arg | Ala | |
| 110 | | | | | 115 | | | | | 120 | | | | | | |

| GAG | CTC | CAA | GAG | GGC | GCG | CGC | CAG | AAG | CTG | CAC | GAG | CTG | CAA | GAG | AAG | 536 |
|---|---|---|---|---|---|---|---|---|---|---|---|---|---|---|---|---|
| Glu | Leu | Gln | Glu | Gly | Ala | Arg | Gln | Lys | Leu | His | Glu | Leu | Gln | Glu | Lys | |
| 125 | | | | 130 | | | | | 135 | | | | | | 140 | |

| CTG | AGC | CCA | CTG | GGC | GAG | GAG | ATG | CGC | GAC | CGC | GCG | CGC | GCC | CAT | GTG | 584 |
|---|---|---|---|---|---|---|---|---|---|---|---|---|---|---|---|---|
| Leu | Ser | Pro | Leu | Gly | Glu | Glu | Met | Arg | Asp | Arg | Ala | Arg | Ala | His | Val | |
| | | | | 145 | | | | | 150 | | | | | | 155 | |

| GAC | GCG | CTG | CGC | ACG | CAT | CTG | GCC | CCC | TAC | AGC | GAC | GAG | CTG | CGC | CAG | 632 |
|---|---|---|---|---|---|---|---|---|---|---|---|---|---|---|---|---|
| Asp | Ala | Leu | Arg | Thr | His | Leu | Ala | Pro | Tyr | Ser | Asp | Glu | Leu | Arg | Gln | |
| | | | 160 | | | | | 165 | | | | | 170 | | | |

| TGC | TTG | GCC | GCG | CGC | CTT | GAG | GCT | CTC | AAG | GAG | AAC | GGC | GGC | GCC | AGA | 680 |
|---|---|---|---|---|---|---|---|---|---|---|---|---|---|---|---|---|
| Cys | Leu | Ala | Ala | Arg | Leu | Glu | Ala | Leu | Lys | Glu | Asn | Gly | Gly | Ala | Arg | |
| | | 175 | | | | | 180 | | | | | 185 | | | | |

| CTG | GCC | GAG | TAC | CAC | GCC | AAG | GCC | ACC | GAG | CAT | CTG | AGC | ACG | CTC | AGC | 728 |
|---|---|---|---|---|---|---|---|---|---|---|---|---|---|---|---|---|
| Leu | Ala | Glu | Tyr | His | Ala | Lys | Ala | Thr | Glu | His | Leu | Ser | Thr | Leu | Ser | |
| | 190 | | | | | 195 | | | | | 200 | | | | | |

| GAG | AAG | GCC | AAG | CCC | GCG | CTC | GAG | GAC | CTC | CGC | CAA | GGC | CTG | CTG | CCC | 776 |
|---|---|---|---|---|---|---|---|---|---|---|---|---|---|---|---|---|
| Glu | Lys | Ala | Lys | Pro | Ala | Leu | Glu | Asp | Leu | Arg | Gln | Gly | Leu | Leu | Pro | |
| 205 | | | | 210 | | | | | 215 | | | | | | 220 | |

| GTG | CTG | GAG | AGC | TTC | AAG | GTC | AGC | TTC | CTG | AGC | GCT | CTC | GAG | GAG | TAC | 824 |
|---|---|---|---|---|---|---|---|---|---|---|---|---|---|---|---|---|
| Val | Leu | Glu | Ser | Phe | Lys | Val | Ser | Phe | Leu | Ser | Ala | Leu | Glu | Glu | Tyr | |
| | | | | 225 | | | | | 230 | | | | | | 235 | |

| | | | | | | | | | | | | |
|---|---|---|---|---|---|---|---|---|---|---|---|---|
| ACT | AAG | AAG | CTC | AAC | ACC | CAG | TG AGGCGCCCGC CGCCGCCCCC CTTCCCGGTG | | | | | 877 |
| Thr | Lys | Lys | Leu | Asn | Thr | Gln | | | | | | |
| | | | | 240 | | | | | | | | |

CTCAGAATAA ACGTTTCCAA AGTGGGAAAA AAAAAAAAAA AAAAAAAAAA AAAAAAAAC     937

TGGATCCGTC GACCTGCAGC CAAGCTT     964

(2) INFORMATION FOR SEQ ID NO:6:

(i) SEQUENCE CHARACTERISTICS:
        (A) LENGTH: 264 amino acids
        (B) TYPE: amino acid
        (D) TOPOLOGY: linear (ii) MOLECULE TYPE: protein (xi) SEQUENCE DESCRIPTION: SEQ ID NO:6:

| Met | Lys | Lys | Thr | Ala | Ile | Ala | Ile | Ala | Val | Ala | Leu | Ala | Gly | Phe | Ala |
|---|---|---|---|---|---|---|---|---|---|---|---|---|---|---|---|
| -21 | -20 | | | | -15 | | | | | -10 | | | | | |
| Thr | Val | Ala | Asn | Ala | Asp | Glu | Pro | Pro | Gln | Ser | Pro | Trp | Asp | Arg | Val |
| -5 | | | | | 1 | | | 5 | | | | | | 10 | |
| Lys | Asp | Leu | Ala | Thr | Val | Tyr | Val | Asp | Val | Leu | Lys | Asp | Ser | Gly | Arg |
| | | | 15 | | | | 20 | | | | | 25 | | | |
| Asp | Tyr | Val | Ser | Gln | Phe | Glu | Gly | Ser | Ala | Leu | Gly | Lys | Gln | Leu | Asn |
| | | 30 | | | | | 35 | | | | | 40 | | | |
| Leu | Lys | Leu | Leu | Asp | Asn | Trp | Asp | Ser | Val | Thr | Ser | Thr | Phe | Ser | Lys |
| | 45 | | | | | 50 | | | | | 55 | | | | |
| Leu | Arg | Glu | Gln | Leu | Gly | Pro | Val | Thr | Gln | Glu | Phe | Trp | Asp | Asn | Leu |
| 60 | | | | | 65 | | | | | 70 | | | | | 75 |
| Glu | Lys | Glu | Thr | Glu | Gly | Leu | Arg | Gln | Glu | Met | Ser | Lys | Asp | Leu | Glu |
| | | | | 80 | | | | | 85 | | | | | 90 | |
| Glu | Val | Lys | Ala | Lys | Val | Gln | Pro | Tyr | Leu | Asp | Asp | Phe | Gln | Lys | Lys |
| | | | 95 | | | | 100 | | | | | 105 | | | |
| Trp | Gln | Glu | Glu | Met | Glu | Leu | Tyr | Arg | Gln | Lys | Val | Glu | Pro | Leu | Arg |
| | | 110 | | | | | 115 | | | | | 120 | | | |
| Ala | Glu | Leu | Gln | Glu | Gly | Ala | Arg | Gln | Lys | Leu | His | Glu | Leu | Gln | Glu |
| | 125 | | | | | 130 | | | | | 135 | | | | |
| Lys | Leu | Ser | Pro | Leu | Gly | Glu | Glu | Met | Arg | Asp | Arg | Ala | Arg | Ala | His |
| 140 | | | | | 145 | | | | | 150 | | | | | 155 |
| Val | Asp | Ala | Leu | Arg | Thr | His | Leu | Ala | Pro | Tyr | Ser | Asp | Glu | Leu | Arg |
| | | | | 160 | | | | | 165 | | | | | 170 | |
| Gln | Cys | Leu | Ala | Ala | Arg | Leu | Glu | Ala | Leu | Lys | Glu | Asn | Gly | Gly | Ala |
| | | | 175 | | | | | 180 | | | | | 185 | | |
| Arg | Leu | Ala | Glu | Tyr | His | Ala | Lys | Ala | Thr | Glu | His | Leu | Ser | Thr | Leu |
| | | 190 | | | | | 195 | | | | | 200 | | | |
| Ser | Glu | Lys | Ala | Lys | Pro | Ala | Leu | Glu | Asp | Leu | Arg | Gln | Gly | Leu | Leu |
| | 205 | | | | | 210 | | | | | 215 | | | | |
| Pro | Val | Leu | Glu | Ser | Phe | Lys | Val | Ser | Phe | Leu | Ser | Ala | Leu | Glu | Glu |
| 220 | | | | | 225 | | | | | 230 | | | | | 235 |
| Tyr | Thr | Lys | Lys | Leu | Asn | Thr | Gln | | | | | | | | |
| | | | | 240 | | | | | | | | | | | |

(2) INFORMATION FOR SEQ ID NO:7:

(i) SEQUENCE CHARACTERISTICS:
        (A) LENGTH: 863 base pairs
        (B) TYPE: nucleic acid
        (C) STRANDEDNESS: both
        (D) TOPOLOGY: both ( i i ) MOLECULE TYPE: cDNA to mRNA ( i x ) FEATURE:
    ( A ) NAME/KEY: sig_peptide
    ( B ) LOCATION: 54..116

( i x ) FEATURE:
    ( A ) NAME/KEY: mat_peptide
    ( B ) LOCATION: 117..847

( i x ) FEATURE:
    ( A ) NAME/KEY: CDS
    ( B ) LOCATION: 54..847

( x i ) SEQUENCE DESCRIPTION: SEQ ID NO:7:

```
GCGGCCGCGG CTAATTGACA TGGCGTATTT TGGATGATAA CGAGGCGCAA AAA ATG                56
                                                            Met
                                                            -21

AAA AAG ACA GCT ATC GCG ATT GCA GTG GCA CTG GCT GGT TTC GCT ACC               104
Lys Lys Thr Ala Ile Ala Ile Ala Val Ala Leu Ala Gly Phe Ala Thr
-20             -15                 -10                 -5

GTA GCG AAC GCG GAC GAG CCA CCG CAG AGC CCA TGG GAT CGA GTG AAG               152
Val Ala Asn Ala Asp Glu Pro Pro Gln Ser Pro Trp Asp Arg Val Lys
            1               5                   10

GAC CTG GCC ACT GTG TAC GTG GAT GTG CTC AAA GAC AGC GGC AGA GAC               200
Asp Leu Ala Thr Val Tyr Val Asp Val Leu Lys Asp Ser Gly Arg Asp
        15                  20                  25

TAT GTG TCC CAG TTT GAA GGC TCC GCC TTG GGA AAA CAG CTA AAC CTA               248
Tyr Val Ser Gln Phe Glu Gly Ser Ala Leu Gly Lys Gln Leu Asn Leu
    30                  35                  40

AAG CTC CTT GAC AAC TGG GAC AGC GTG ACC TCC ACC TTC AGC AAG CTG               296
Lys Leu Leu Asp Asn Trp Asp Ser Val Thr Ser Thr Phe Ser Lys Leu
45                  50                  55                  60

CGC GAA CAG CTC GGC CCT GTG ACC CAG GAG TTC TGG GAT AAC CTG GAA               344
Arg Glu Gln Leu Gly Pro Val Thr Gln Glu Phe Trp Asp Asn Leu Glu
                65                  70                  75

AAG GAG ACA GAG GGC CTG AGG CAG GAG ATG AGC AAG GAT CTG GAG GAG               392
Lys Glu Thr Glu Gly Leu Arg Gln Glu Met Ser Lys Asp Leu Glu Glu
            80                  85                  90

GTG AAG GCC AAG GTG CAG CCC TAC CTG GAC GAC TTC CAG AAG AAG TGG               440
Val Lys Ala Lys Val Gln Pro Tyr Leu Asp Asp Phe Gln Lys Lys Trp
        95                  100                 105

CAG GAG GAG ATG GAG CTC TAC CGC CAG AAG GTG GAG CCG CTG CGC GCA               488
Gln Glu Glu Met Glu Leu Tyr Arg Gln Lys Val Glu Pro Leu Arg Ala
110                 115                 120

GAG CTC CAA GAG GGC GCG CGC CAG AAG CTG CAC GAG CTG CAA GAG AAG               536
Glu Leu Gln Glu Gly Ala Arg Gln Lys Leu His Glu Leu Gln Glu Lys
125                 130                 135                 140

CTG AGC CCA CTG GGC GAG GAG ATG CGC GAC CGC GCG CGC GCC CAT GTG               584
Leu Ser Pro Leu Gly Glu Glu Met Arg Asp Arg Ala Arg Ala His Val
                145                 150                 155

GAC GCG CTG CGC ACG CAT CTG GCC CCC TAC AGC GAC GAG CTG CGC CAG               632
Asp Ala Leu Arg Thr His Leu Ala Pro Tyr Ser Asp Glu Leu Arg Gln
            160                 165                 170

TGC TTG GCC GCG CGC CTT GAG GCT CTC AAG GAG AAC GGC GGC GCC AGA               680
Cys Leu Ala Ala Arg Leu Glu Ala Leu Lys Glu Asn Gly Gly Ala Arg
        175                 180                 185

CTG GCC GAG TAC CAC GCC AAG GCC ACC GAG CAT CTG AGC ACG CTC AGC               728
Leu Ala Glu Tyr His Ala Lys Ala Thr Glu His Leu Ser Thr Leu Ser
    190                 195                 200

GAG AAG GCC AAG CCC GCG CTC GAG GAC CTC CGC CAA GGC CTG CTG CCC               776
Glu Lys Ala Lys Pro Ala Leu Glu Asp Leu Arg Gln Gly Leu Leu Pro
205                 210                 215                 220
```

```
GTG CTG GAG AGC TTC AAG GTC AGC TTC CTG AGC GCT CTC GAG GAG TAC          824
Val Leu Glu Ser Phe Lys Val Ser Phe Leu Ser Ala Leu Glu Glu Tyr
                225                 230                 235

ACT AAG AAG CTC AAC ACC CAG TA ATAAGGATCC AAGCTT                          863
Thr Lys Lys Leu Asn Thr Gln
                240
```